US00PP18570P2

(12) United States Plant Patent
Olsthoorn

(10) Patent No.: US PP18,570 P2
(45) Date of Patent: Mar. 11, 2008

(54) ***SPATHIPHYLLUM* PLANT NAMED '98216-59'**

(50) Latin Name: *Spathiphyllum Schott.*
Varietal Denomination: 98216-59

(75) Inventor: Petrus C. M. Olsthoorn, Honselersdijk (NL)

(73) Assignee: P.C.M. Olsthoorn Holding BV, Honselersdijk (NL)

( * ) Notice: Subject to any disclaimer, the term of this patent is extended or adjusted under 35 U.S.C. 154(b) by 0 days.

(21) Appl. No.: 11/580,783

(22) Filed: Oct. 13, 2006

(51) Int. Cl.
*A01H 5/00* (2006.01)

(52) U.S. Cl. ..... Plt./364

(58) Field of Classification Search ..... Plt./364
See application file for complete search history.

*Primary Examiner*—Kent Bell
*Assistant Examiner*—Annette H Para

(57) ABSTRACT

A new cultivar of *Spathiphyllum* plant named '98216-59' that is characterized by vertical white spathes, dark green leaves and a medium spathe size.

1 Drawing Sheet

Botanical classification: *Spathiphyllum Schott.*
Variety denomination: '98216-59'.

BACKGROUND OF THE INVENTION

The present invention relates to a new and distinct cultivar of *Spathiphyllum* plant botanically known as *Spathiphyllum Schott.* and hereinafter referred to by the cultivar name '98216-59'.

'98216-59' is a hybrid that originated from the hybridization of the female or seed parent a proprietary *Spathiphyllum Schott.* identified as 98338-63 (not patented) and the male or pollen parent a proprietary *Spathiphyllum Schott.* identified as 96361-5 (not patented). The cultivar '98216-59' was selected by the inventor in February of 1999 as a single plant within the progeny of the stated cross in Honselersdijk, The Netherlands.

Asexual reproduction by tissue culture of the new cultivar '98216-59' was first performed in February of 2001 in Honselersdijk, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Spathiphyllum* cultivar '98216-59'.

1. *Spathiphyllum* '98216-59' exhibits white spathes.
2. *Spathiphyllum* '98216-59' exhibits dark green leaves.
3. *Spathiphyllum* '98216-59' exhibits a medium spathe size.
4. *Spathiphyllum* '98216-59' exhibits vertical spathes.

The closest comparison cultivar is *Spathiphyllum* 'Sweet Pablo' (U.S. plant Pat. No. PP10,817). The new cultivar '98216-59' is distinguishable from 'Sweet Pablo' by the following characteristics:

1. '98216-59' has narrower leaves than those of 'Sweet Pablo'.
2. '98216-59' has darker green leaves than those of 'Sweet Pablo'.

The new cultivar '98216-59' is distinguishable from the male parent *Spathiphyllum* '96361-5' in having more vertical spathes and narrower leaves. The new cultivar '98216-59' is distinguishable from the female parent *Spathiphyllum* '98338-63' in having more vertical spheres.

BRIEF DESCRIPTION OF THE DRAWING

The accompanying photograph illustrates the distinguishing traits of *Spathiphyllum* '98216-59'. The plant in the photograph shows an overall view of a 29 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Spathiphyllum* cultivar named '98216-59'. Data was collected in Honselersdijk, The Netherlands from 29 week old greenhouse grown plants in 2 liter containers. The time of year was Spring and the average temperature was 22 degrees Centigrade during the day and 20 degrees Centigrade at night. No photoperiodic treatments were used. 150 PPM of Gibberallic acid was applied for flower initiation. Color determinations are in accordance with The Royal Horticultural Society Colour Chart 2001 edition, except where general color terms of ordinary dictionary significance are used. The growing requirements are similar to the species. '98216-59' has not been tested under all possible conditions and phenotypic differences may be observed with variations in environmental, climatic, and cultural conditions, however, without any variance in genotype.

Botanical classification: *Spathiphyllum Schott.* '98216-59'.
Use: Ornamental.

Parentage: '98216-59' is a hybrid plant that resulted from the hybridization of the following parent plants:

*Female parent.*—A proprietary *Spathiphyllum Schott.* identified as '98338-63'.

*Male parent.*—A proprietary *Spathiphyllum Schott.* identified as '96361-5'.

Vigor: Moderate.
Growth rate: Moderate.
Growth habit: Moderately branching from base, bushy and dense.
Plant shape: Inverted triangle with inflorescences on top.
Suitable container size: 2 Liter container.
Height: Average 54 cm to top of leaf plane, 78.5 cm to top of inflorescences.
Width: Average 66 cm in width.
Hardiness: USDA Zone 10.
Propagation: Tissue Culture.
Time to initiate roots (summer and winter): Approximately 14 days to produce roots on an initial cutting.
Time to produce a rooted cutting or liner (summer and winter): Approximately 38 days.
Root system: Fine and fibrous.
Stem: No stems, Leaves grow directly from base, Average 8 clumps, clump color 144A.
Foliage:
*Texture.*—Smooth, slightly leathery.
*Appearance.*—Glossy.
*Leaf arrangement.*—Alternate.
*Compound or single.*—Single.
*Leaf shape.*—Elliptic.
*Leaf apex.*—Apiculate.
*Leaf base.*—Attenuate.
*Leaf length.*—Average 29 cm in length.
*Leaf width.*—12.5 cm in width.
*Quantity of leaves per clump.*—Average 6.
*Pubescence.*—Absent.
*Leaf margin.*—Entire, slightly wavy.
*Vein pattern.*—Pinnate.
*Young leaf color* (*upper surface*).—141A to 143A.
*Young leaf color* (*lower surface*).—137C to 137D to 138B.
*Mature leaf color* (*upper surface*).—139A.
*Mature leaf color* (*lower surface*).—137B.
*Vein color* (*lower surface*).—144A to 144B.
*Vein color* (*upper surface*).—141A.
*Leaf attachment.*—Petiolate.
*Petiole dimensions.*—Average 26.1 cm in length excluding geniculum, 3.5 mm in diameter below geniculum to 6 mm in diameter above clump.
*Petiole aspect.*—Round.
*Petiole color.*—144A to 144B, darker towards the top 137A to 141A.
*Geniculum dimensions.*—Average 3.9 cm in length and 4.5 mm in diameter.
*Geniculum aspect.*—Rounded, glossy, glabrous.
*Geniculum color.*—143B to 143C.
*Petiole sheath dimensions.*—Average 19.3 cm in length and 6 mm in diameter.
*Petiole sheath color.*—144A.
*Durability of foliage to stress.*—High.
Inflorescence:
*Inflorescence arrangement.*—Spathes with spadices held above the foliage on erect peduncles arising from the petiole sheath.
*Flowering habit.*—Continuous.
*Quantity of spathes per plant.*—Average 4.
*Natural flowering season.*—Autumn to winter to spring.
*Time to flower or response time.*—26 weeks.
*Fragrance.*—Moderate to strong, sweet.
*Self-cleaning or persistent.*—Persistent.
*Flower longevity.*—Lasts approximately 3 weeks on plant.
*Spathe aspect.*—Slightly cupped.
*Spathe dimensions.*—Average 19.8 cm in length, 9 cm in width and 5.7 cm in depth.
*Spathe texture.*—Glabrous, slightly leathery.
*Spathe shape.*—Elliptic.
*Spathe margin.*—Entire.
*Spathe apex.*—Apiculate.
*Spathe base.*—Cuneate.
*Spathe color when opening* (*front side*).—155C, apex 143B to 143C.
*Spathe color when opening* (*rear side*).—155C, apex 143B to 143C.
*Spathe color when fully opened* (*front side*).—155C, apex 143B to 143C.
*Spathe color when fully opened* (*rear side*).—155C, apex 143B to 143C.
*Spathe color fading to.*—Not fading.
*Spadix shape.*—Columnar, arising from top of peduncle.
*Spadix tip.*—Obtuse.
*Spadix base.*—Obtuse.
*Spadix dimensions.*—Average 5.9 cm in length and 1.6 mm in diameter.
*Spadix color when opening.*—158A to 158B.
*Spadix color when fully opened.*—158B.
*Quantity of flowers per spadix.*—Average 140.
*Spadix flower arrangement.*—Bisexual, rounded.
*Spadix flower dimensions.*—3.5 mm in diameter and 3 mm in depth. Reproductive organs:
*Anther color.*—158D.
*Amount of pollen.*—Moderate.
*Pollen color.*—158D.
*Stigma color.*—158B.
*Ovary color.*—158B.
Peduncle:
*Peduncle dimensions.*—Average 59.4 cm in length and 6.0 mm. in diameter.
*Peduncle angle.*—5 degrees from vertical.
*Peduncle color.*—137D.
*Peduncle strength.*—*Strong.*
Seed: Seed production has not been observed.
Disease and insect resistance: Plants of the new *Spathiphyllum* have not been observed for disease or insect resistance.

It is claimed:

1. A new and distinct variety of *Spathiphyllum* plant named '98216-59' as described and illustrated.

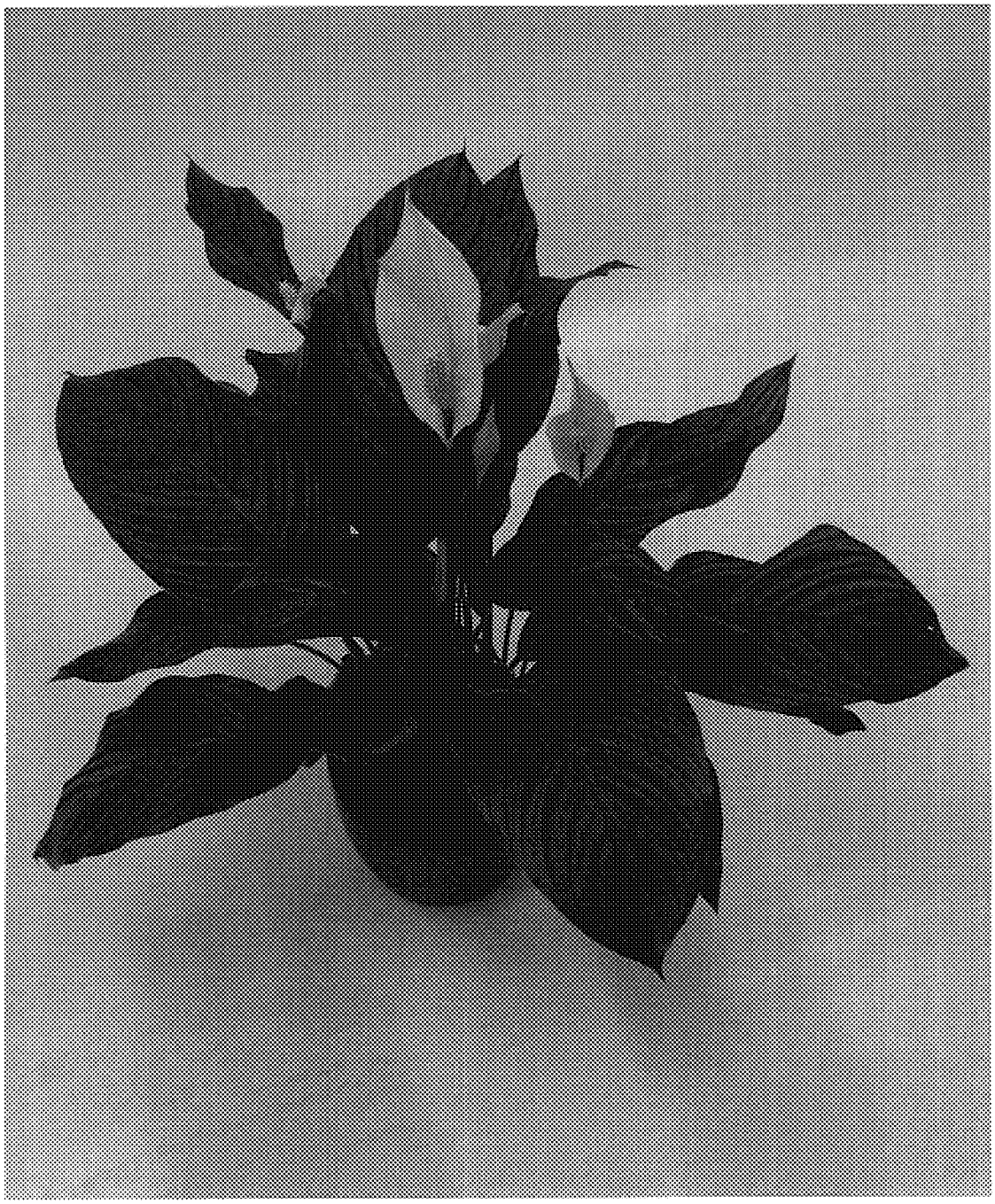

* * * * *